(12) United States Patent
Taira (10) Patent No.: US 10,085,644 B2
(45) Date of Patent: Oct. 2, 2018

(54) OPTICAL IMAGING SYSTEM (75) Inventor: Kenji Taira, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 815 days.

(21) Appl. No.: 13/821,138

(22) PCT Filed: Sep. 7, 2011

(86) PCT No.: PCT/JP2011/005036
§ 371 (c)(1),
(2), (4) Date: Jul. 27, 2015

(87) PCT Pub. No.: WO2012/032779
PCT Pub. Date: Mar. 15, 2012

(65) Prior Publication Data
US 2015/0335247 A1 Nov. 26, 2015

(30) Foreign Application Priority Data
Sep. 7, 2010 (JP) .............................. 2010-199995

(51) Int. Cl.
| | | |
|---|---|---|
| *A61B 6/00* | (2006.01) | |
| *A61B 5/00* | (2006.01) | |
| *A61B 1/00* | (2006.01) | |
| *A61B 1/06* | (2006.01) | |
| *A61B 90/20* | (2016.01) | |

(52) U.S. Cl.
CPC ........ *A61B 5/0062* (2013.01); *A61B 1/00172* (2013.01); *A61B 1/06* (2013.01); *A61B 5/0066* (2013.01); *A61B 90/20* (2016.02); *A61B 5/7257* (2013.01); *A61B 2576/00* (2013.01)

(58) Field of Classification Search
CPC ............................ A61B 5/0062; A61B 5/0066
See application file for complete search history.

(56) References Cited

U.S. PATENT DOCUMENTS

| | | | |
|---|---|---|---|
| 7,231,243 B2 | 6/2007 | Tearney et al. | |
| 2003/0004412 A1* | 1/2003 | Izatt ................... | A61B 5/0066 600/425 |
| 2005/0168751 A1* | 8/2005 | Horii ................... | A61B 5/0062 356/479 |

(Continued)

FOREIGN PATENT DOCUMENTS

JP          2004-512538 A          4/2004

OTHER PUBLICATIONS

Elsner, A. E., et al. "Detecting AMD with Multiply Scattered Light Tomography", International Ophthalmology, Jul. 2001, vol. 23, Nos. 4-6 pp. 245-250.

(Continued)

*Primary Examiner* — Joel F Brutus
(74) *Attorney, Agent, or Firm* — Scully, Scott, Murphy & Presser, P.C.

(57) ABSTRACT

Provided is an optical imaging system which visualizes a deep portion of a scattering body. The optical imaging system generates an image of an object to be inspected by removing a signal resulting from light reflected and scattered once by a surface of the object to be inspected from the signal obtained by means of an optical system analogous to Optical Coherence Tomography, thereby extracting a signal resulting from multiply scattered light.

11 Claims, 9 Drawing Sheets

(56) References Cited

U.S. PATENT DOCUMENTS

| | | | | |
|---|---|---|---|---|
| 2007/0064239 A1* | 3/2007 | Fujita | ................ | G02B 21/0056 356/479 |
| 2007/0076211 A1* | 4/2007 | Toida | ................ | G01B 9/02004 356/456 |
| 2008/0079949 A1* | 4/2008 | Kuroiwa | ............ | G01B 9/02004 356/496 |
| 2008/0137094 A1* | 6/2008 | Teramura | ........... | G01B 9/02004 356/489 |

OTHER PUBLICATIONS

Boas, D.A., et al. "Imaging the Body with Diffuse Optical Tomography", IEEE Signal Processing Magazine, Nov. 2011, vol. 18, Issue 6, pp. 57-75.

Elsner, A. E., et al. "Multiply Scattered Light Tomography and Confocal Imaging: Detecting Neovascularization in Age-Related Macular Degeneration", Optics Express, Jul. 17, 2000, vol. 7, No. 2, pp. 95-106.

Mukaigawa, Y., et al. "Analysis of Light Transport in Scattering Media", Meeting on Image Recognition and Understanding (MIRU2010), Jul. 2010, pp. 665-672, together with an English language abstract.

Huang, D., et al. "Optical Coherence Tomography", Science, New Series, Nov. 22, 1991, vol. 254, No. 5035, pp. 1178-1181.

International Search Report PCT/JP2011/005036 dated Dec. 6, 2011.

* cited by examiner

OPTICAL IMAGING SYSTEM

CROSS-REFERENCE TO RELATED APPLICATION

This application claims priority to Japanese Patent Application No. 2010-199995, filed on Sep. 7, 2010, the content of which is incorporated herein by reference in its entirety.

TECHNICAL FIELD

The present invention relates to an in vivo optical imaging system.

BACKGROUND ART

Optical Coherence Tomography (OCT) is widely accepted as a technique for acquiring tomographic images of a living body (see Non-Patent Document 1). OCT is a technique with significant potential for in vivo provision of morphological information having a spatial resolution of about 1 to 10 μm in a depth direction noninvasively and without exposure to harmful radiation.

In OCT, light reflected or scattered once within a biological sample is detected. The detection is conducted by means of a Michelson interferometer configuration, in which an interference component of light returned from the living body (hereinafter referred to as inspection light) and reference light is used as a signal. If relative delay time, between the inspection light and the reference light is within the coherence time of a light source, a stable interference signal can be obtained. OCT utilizes the stable interference signal.

RELATED ART DOCUMENT

Non-Patent Document 1: Huang et al., Science, vol. 254, p. 1178 (1991)

DISCLOSURE OF THE INVENTION

Problems to be Solved by the Invention

Although OCT is a very attractive technique as described above, it is characterized by a very limited observable penetration depth of about 1 to 2 mm from a surface of a biological sample. This is because a living body has a strong light scattering property. Most of the light applied to the living body undergoes multiple scattering while propagating 1 to 2 mm in vivo. Since inspection light subjected to multiple scattering cannot generate a stable interference signal with reference light, it is not possible to detect the inspection light in OCT.

There are great needs for knowing a condition of a deep portion of the living body, such as ascertainment of positions or conditions of blood vessels, nerves, and lymph vessels, diagnosis of the degree of invasion of cancers, etc. in vivo, noninvasively, and without exposure to radiation. However, it is not possible to meet these needs by OCT due to the characteristic mentioned above.

SUMMARY OF THE INVENTION

The invention of an optical imaging system according to a first aspect for achieving the object mentioned above comprises:

a light generation unit for emitting light;

an optical multiplex/demultiplex unit for demultiplexing the light from the light generation unit into inspection light and reference light so as to guide the inspection light to an object to be inspected and the reference light to a light reflection unit, and multiplexing reflected inspection light obtained by the inspection light being reflected and scattered by the object to be inspected and reflected reference light obtained by the reference light being reflected by the light reflection unit so as to generate interference light;

a scanning unit for scanning the inspection light on the object to be inspected;

a photoelectric conversion unit for receiving the interference light generated by the optical multiplex/demultiplex unit and photoelectrically converting the interference light;

an analog-digital conversion unit for converting an analog output signal from the photoelectric conversion unit to a digital signal;

a signal processing unit for removing a signal resulting from the light reflected and scattered once by the object to be inspected from the output signal from the analog-digital conversion unit, thereby extracting a signal resulting from multiply scattered light in the object to be inspected and integrating the extracted signal; and an image processing unit for generating an image of the object to be inspected on the basis of an output signal from the signal processing unit and scanning information from the scanning unit.

The invention according to a second aspect is an optical imaging system according to the first aspect, wherein the light generation unit is a wavelength swept laser.

The invention according to a third aspect is an optical imaging system according to the second aspect, wherein the signal processing unit comprises:

a signal conversion unit for performing Fourier transform of the output signal from the analog-digital conversion unit and outputting a signal representative of a signal intensity distribution with respect to a position in the object to be inspected;

a signal extraction unit for extracting the signal resulting from multiply scattered light in the object to be inspected from the output signal from the signal conversion unit; and an integration unit for calculating and outputting an integrated value of the output signal from the signal extraction unit.

The invention according to a fourth aspect is an optical imaging system according to the first aspect, wherein the light generation unit is a super luminescent diode or pulse light source, and the light reflection unit is driven in such a way that the light reflection unit sweeps over relative delay time between the inspection light and the reference light.

The invention according to a fifth aspect is an optical imaging system according to the fourth aspect, wherein the signal processing unit comprises:

an envelope detection unit for detecting an envelope of the output signal from the analog-digital conversion unit;

a signal extraction unit for extracting the signal resulting from multiply scattered light in the object to be inspected from the output signal from the envelope detection unit; and an integration unit for calculating and outputting an integrated value of the output signal from the signal extraction unit.

The invention according to a sixth aspect is an optical imaging system according to the third or fifth aspect, wherein the signal extraction unit extracts a portion of the output signal of the signal conversion unit corresponding to a position 1.5 mm or more, in physical length in a depth direction of the object to be inspected, apart from a position on the object to be inspected with the highest signal strength.

The invention according to a seventh aspect is an optical imaging system according to the first aspect, wherein the light generation unit is a super luminescent diode or pulse light source, and the light reflection unit is set in such a way that delay time of the reference light coincides with delay time of the multiply scattered light.

The invention according to an eighth aspect is an optical imaging system according to the seventh aspect, wherein the signal processing unit comprises:

an envelope detection unit for detecting an envelope of the output signal from the analog-digital conversion uni; and an envelope detection output integration unit for calculating an integrated value of the output signal of the envelope detection unit.

The invention according to a ninth aspect is an optical imaging system according to the first aspect, wherein the photoelectric conversion unit performs balanced detection.

Further, the invention of an optical imaging method according to a tenth aspect for achieving the object mentioned above comprises:

a light generation step for emitting light;

an optical multiplexing/demultiplexing step for demultiplexing the light from the light generation step into inspection light and reference light so as to guide the inspection light to an object to be inspected and the reference light to a light reflection unit, and multiplexing reflected inspection light obtained by the inspection light being reflected and scattered by the object to be inspected and reflected reference light obtained by the reference light being reflected by the light reflection unit so as to generate interference light;

a scanning step for scanning the inspection light on the object to be inspected;

a photoelectric conversion step for receiving the interference light generated by the optical multiplexing/demultiplexing step and photoelectrically converting the interference light;

an analog-digital conversion step for converting an analog output signal of the photoelectric conversion step to a digital signal;

a signal processing step for removing a signal resulting from the light reflected and scattered once by the object to be inspected from the output signal in the analog-digital conversion step, thereby extracting a signal resulting from multiply scattered light in the object to be inspected and integrating the extracted signal; and an image processing step for generating an image of the object to be inspected on the basis of the output signal from the signal processing step and scanning information from the scanning step.

The invention of an endoscope according to an eleventh aspect for achieving the object mentioned above is an endoscope for detecting light to be detected from the inside of a body cavity so as to observe the inside of the body cavity, wherein the endoscope comprises the optical imaging system according to any one of the first to ninth aspects, and the endoscope is configured to image the light to be detected from the inside of the body cavity by means of the optical imaging system.

Further, the invention of a microscope according to a twelfth aspect for achieving the object mentioned above is a microscope for detecting light to be detected from an observation sample, wherein the microscope comprises the optical imaging system according to any one of the first to ninth aspects, and the endoscope is configured to image the light to be detected from the observation sample by means of the optical imaging system.

Effect of the Invention

Since reflected light and light scattered once are removed and multiply scattered light is detected for imaging, a condition of a deep portion of a living body can be visualized in vivo, noninvasively, and without exposure to radiation.

BEST MODES FOR CARRYING OUT THE INVENTION

Hereinafter, embodiments of the present invention will be described with reference to the drawings.

(First Embodiment)

Figure 1:
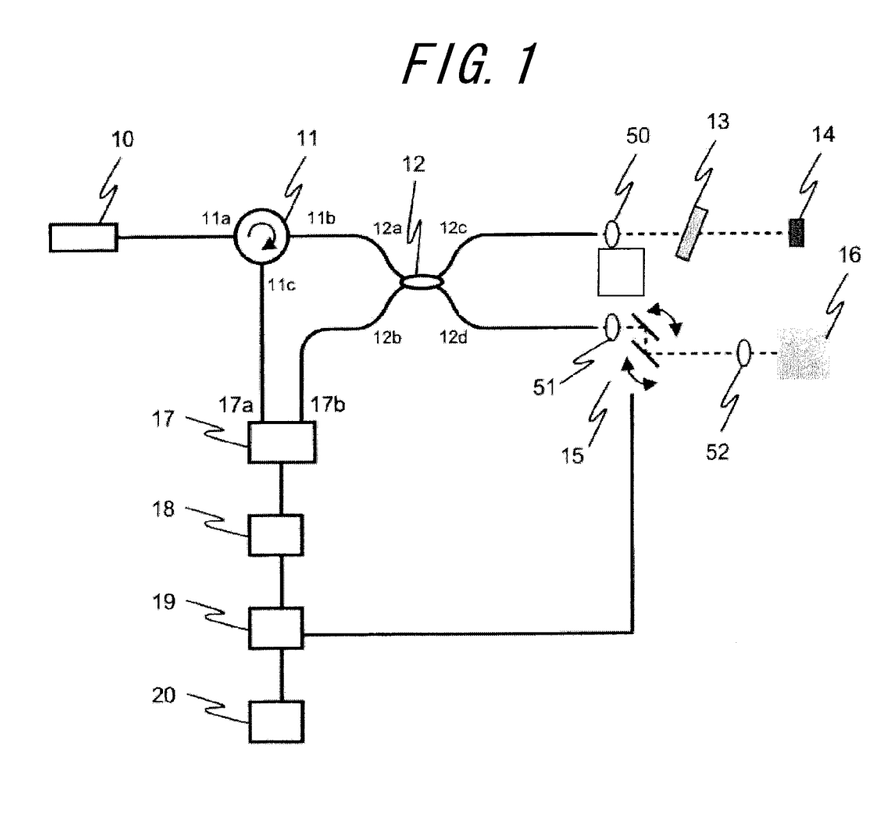
FIG. 1 is a block diagram illustrating a configuration of a main part of an optical imaging system according to a first embodiment of the present invention.

FIG. 1 is a block diagram illustrating a configuration of an optical imaging system according to a first embodiment of the present invention.

In this embodiment, a wavelength swept laser 10 to be used here has a center wavelength of 1030 nm, a sweep wavelength width of 0.4 nm, an average light intensity of 5 mW, and a sweep frequency of 50 kHz. It may be realized by means of a Fourier domain mode locked laser (FDML) (see US 2006/0187537 A1). In doing so, the wavelength swept laser 10 is used in such a way that it does not have a pulsed output time waveform.

The wavelength swept laser 10 has an output end connected to a first port 11a of an optical circulator 11, which includes the first port 11a to a third port 11c. The optical circulator 11 outputs light input from the first port 11a to the second port 11b, and outputs light input to the second port 11b to the third port 11c.

The second port 11b of the optical circulator 11 is connected to a first port 12a of an optical coupler 12, which includes the first port 12a to a fourth port 12d. The optical coupler 12 demultiplexes light input to the first port 12a to the third port 12c and the fourth port 12d with an intensity ratio of 50:50, respectively. Here, the optical coupler 12 functions as an optical multiplex/demultiplex unit for demultiplexing the light from the light generation unit into inspection light and reference light so as to guide the inspection light to an object to be inspected and the reference light to a light reflection unit, and multiplexing reflected inspection light obtained by the inspection light being reflected and scattered by the object to be inspected and reflected reference light obtained by the reference light being reflected by the light reflection unit so as to generate interference light. This optical multiplex/demultiplex unit does not need to be realized as a unitary configuration like the optical coupler 12, but may consist of separate optical coupler members as a demultiplexer and a multiplexer.

Light output from the third port 12c of the optical coupler 12 is used as the reference light. The light output from the third port 12c of the optical coupler 12 is converted to collimated light by a lens 50 and emitted into the air. The emitted reference light is attenuated by an optical attenuator 13 to have a desired light intensity and then reflected by a reflective mirror 14. The reference light reflected by the reflective mirror 14 is input, as the reflected reference light, again through the optical attenuator 13 and the lens 50 and to the third port 12c of the optical coupler 12.

In contrast, the fourth port 12d of the optical coupler 12 is used for the inspection light. The light output from the fourth port 12d of the optical coupler 12 is converted to collimated light by a lens 51 and emitted into the air. The emitted inspection light is two-dimensionally scanned in a propagation direction by an X-Y galvano scanner mirror 15 and collected by a lens 52 on an object to be inspected 16 such as a living body and the like.

The X-Y galvano scanner mirror 15 is controlled in accordance with a signal from a computer 19. The inspection light reflected and scattered in the surface and the inside of the object to be inspected 16 is input, as the reflected inspection light, again through the lens 52, the X-Y galvano scanner mirror 15, and the lens 51 to the fourth port 12d of the optical coupler 12.

The reflected reference light input to the third port 12c of the optical coupler 12 and the reflected inspection light input to the fourth port 12d of the optical coupler 12 interfere with each other at the optical coupler 12, and is output as interference light from the first port 12a and the second port 12b. Here, the interference light output from the first port 12a and the interference light output from the second port 12b have a phase opposite from each other.

On the one hand, the interference light output from the first port 12a of the optical coupler 12 passes through the second port 11b and the third port 11c of the optical circulator 11 and is input to a first port 17a of a balanced receiver 17 as a photoelectric conversion unit. On the other hand, the interference light output from the second port 12b of the optical coupler 12 is input to a second port 17b of the balanced receiver 17. Thus, the balanced receiver 17 photoelectrically converts interference light input respectively to the first port 17a and the second port 17b to obtain an analog signal in which direct-current components have been cancelled and only interference components (alternating-current components) are existent. The balanced receiver 17 to be used here includes two InGaAs photodiodes and a differential amplifier, and has an electric response band of 80 MHz, for example.

The analog signal output from the balanced receiver 17 is input to an analog-to-digital (AD) converter 18 and converted to a digital signal. It is noted that the AD converter 18 to be used here is one with 14 bits and 125 MS/s, for example. The digital output signal from the AD converter 18 is input to the computer 19. The computer 19 performs an operation for generating an image from the signal from the AD converter 18 and positional information from the X-Y galvano scanner mirror 15, and then displays the result on a monitor 20.

Figure 2:
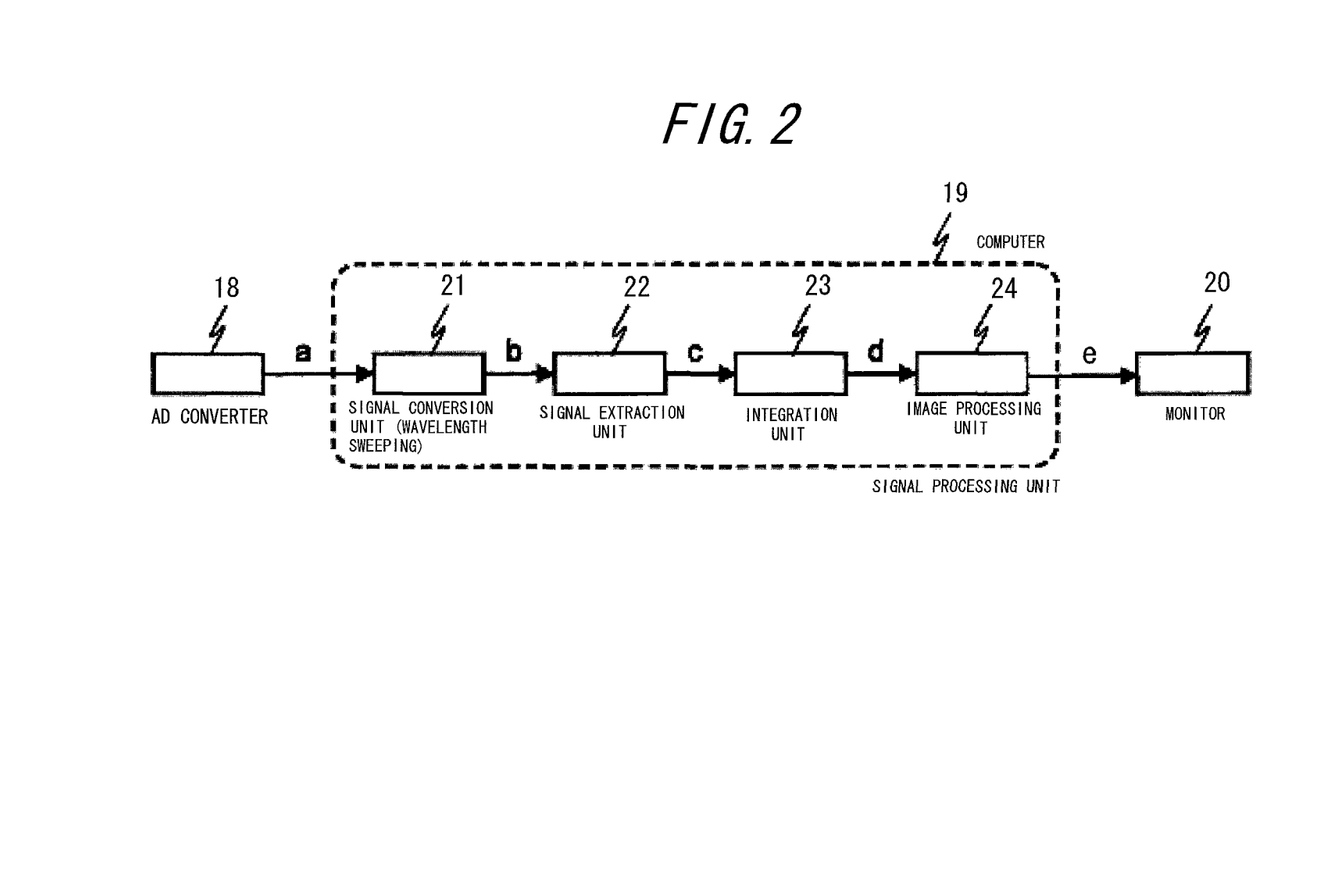
FIG. 2 is a functional block diagram illustrating signal processing performed by a computer illustrated in FIG. 1.

FIG. 2 is a functional block diagram illustrating signal processing performed by the computer 19. Examples of the signal at points a to e in FIG. 2 are shown as a to e, respectively, in FIG. 3, and the signal processing performed by the computer 19 is described below.

Figure 3:
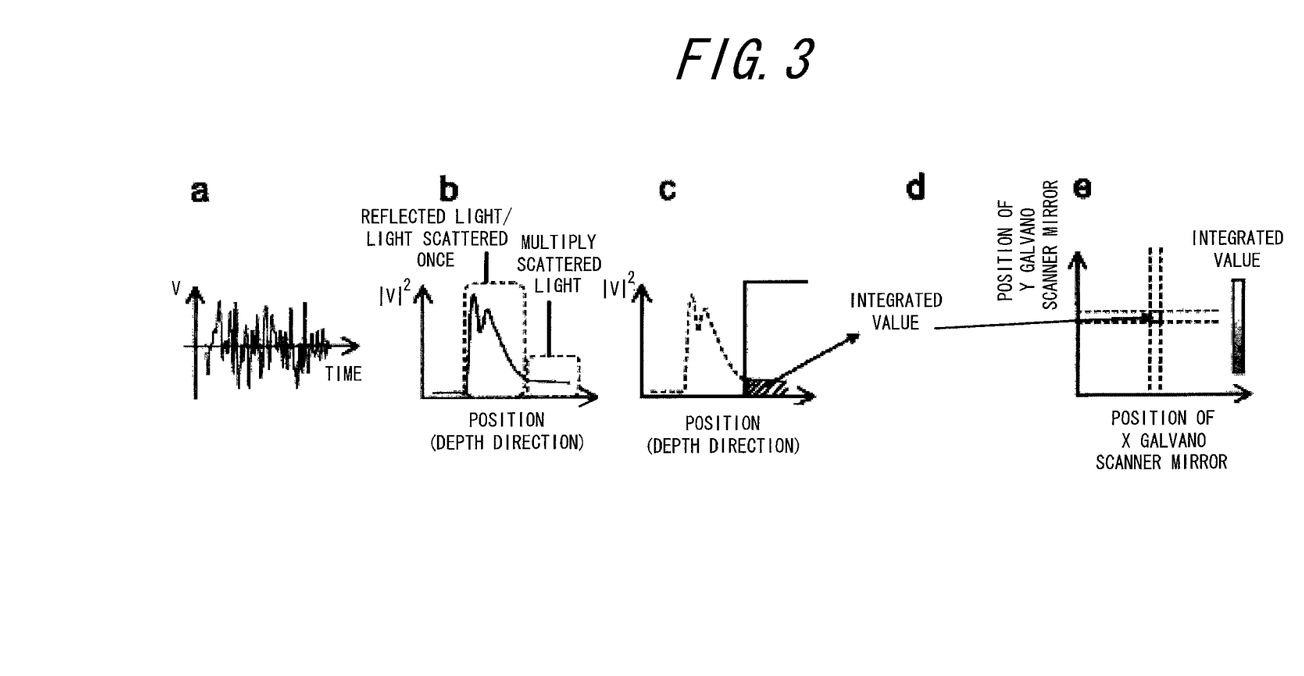
FIG. 3 is a schematic diagram illustrating a signal processing operation illustrated in FIG. 2.

The computer 19 functions as a signal conversion unit (wavelength sweeping) 21, a signal extraction unit 22, an integration unit 23, and an image processing unit 24, and performs the signal processing described below. The signal conversion unit (wavelength sweeping) 21 performs Fourier transform of a digital output signal (FIG. 3, a) from the AD converter 18 to calculate a power spectrum. The frequency is converted from a wavelength sweeping rate of the wavelength swept laser 10 to a spatial distance in a depth direction of the object to be inspected 16, and the power is converted to a reflected and scattered light intensity in each depth position in the object to be inspected 16 for output (FIG. 3, b). The output signal from the signal conversion unit (wavelength sweeping) 21 is input to the signal extraction unit 22. The signal extraction unit 22 removes a signal resulting from the light reflected and scattered once by the object to be inspected 16, thereby extracting a signal resulting from multiply scattered light in the object to be inspected 16 (FIG. 3, c, shaded area). If the object to be inspected 16 is the living body, to be specific, the signal extraction unit 22 is operated to extract a portion of the output signal of the signal conversion unit 21 corresponding to a position 1.5 mm or more in a depth direction apart from a position with the highest signal strength. The output of the signal extraction unit 22 is input to the integration unit 23. The integration unit 23 is operated to integrate a signal received from the signal extraction unit 22 in terms of positions, and outputs the integrated value (FIG. 3, d). The output signal from the integration unit 23 is input to the image processing unit 24. The image processing unit 24 assigns an output value from the integration unit 23 to each set value of the X-Y galvano scanner mirror 15, that is, each position on the object to be inspected 16 irradiated with the inspection light, and generates an image with information on the deep portion of the object to be inspected 16 (FIG. 3, e). Output from the image processing unit 24 is input to the monitor 20, as a result of which the image with information on the deep portion of the object to be inspected 16 is displayed on the monitor 20. In this way, a topographic image of the deep portion of the living body can be obtained.

Thus, this embodiment makes it possible to remove the signal resulting from the light reflected and scattered once by the object to be inspected from the output signal from the AD converter 18, thereby taking out and integrating the signal resulting from the multiply scattered light in the object to be inspected. As a result, information from the deep portion of the object to be inspected 16 can be imaged efficiently.

Further, in this embodiment, the optical spectrum band of the wavelength swept laser 10 has a wavelength width of 0.4 nm, which is set to be significantly narrower than for the typical OCT. This is because narrower wavelength bandwidth of the wavelength swept laser 10 is expected to offer more improved detection sensitivity for detecting the multiply scattered light. For this reason, the optical spectrum width of the wavelength swept laser 10 is reduced to the extent that it has a spatial resolution enough to separate the surface portion (at a depth of about 1.5 mm or less in the living body) and the deep portion (at a depth of about 1.5 mm or more in the living body) of the object to be inspected 16. In this way, the detection sensitivity can be optimized.

Further, in this embodiment, it is possible to use an optical fiber portion for guiding the inspection light (optical fiber connected to the fourth port 12b of the optical coupler 12) in an endoscope. With an endoscope configuration, it is possible to assist surgical operations by diagnosing the degree of invasion of cancers, visualizing blood vessels, nerves, and lymph vessels which are covered with fat, etc.

(Second Embodiment)

Figure 4:
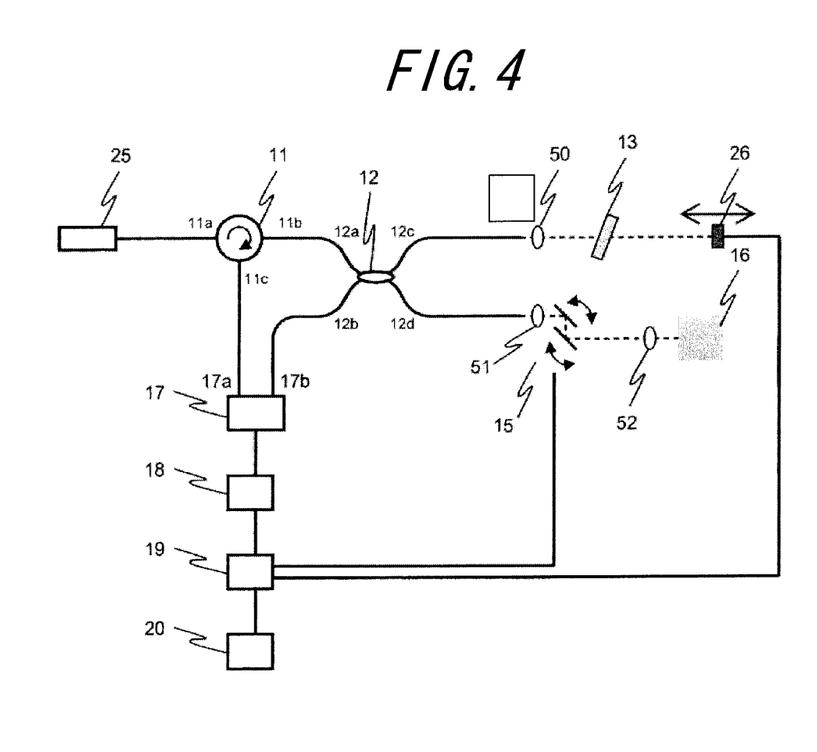
FIG. 4 is a block diagram illustrating a configuration of a main part of an optical imaging system according to a second embodiment of the present invention.

FIG. 4 is a block diagram illustrating a configuration of the optical imaging system according to a second embodiment of the present invention.

FIG. 4 is similar to FIG. 1, except that a super luminescent diode (SLD) 25 and a movable reflective mirror 26 are used in FIG. 4. The SLD 25 to be used here has a wavelength range of 1045 nm to 1055 nm and an average optical output of 10 mW. The movable reflective light 26 is controlled in accordance with the signal from the computer 19 in such a way that it sweeps over relative delay time between the inspection light and the reference light. Since the configuration is otherwise similar to that illustrated in FIG. 1, the same components are denoted by the same reference symbols, and the description thereof will be omitted.

Figure 5:
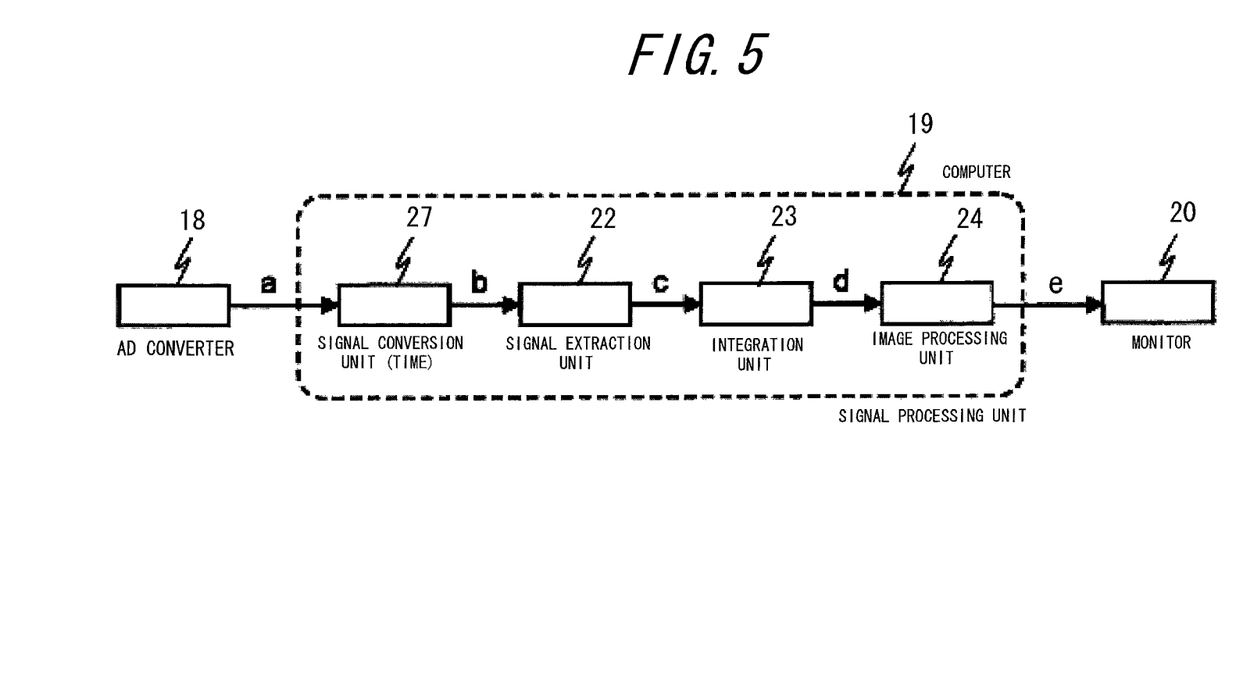
FIG. 5 is a functional block diagram illustrating signal processing performed by a computer illustrated in FIG. 4.

The signal processing performed by the computer 19 in FIG. 4 is illustrated in FIG. 5. FIG. 5 is similar to FIG. 2, except that signal conversion unit (time) 27 is used in FIG. 5. Examples of the signal at points a to e in FIG. 5 are shown as a to e, respectively, in FIG. 6, and the signal processing performed by the computer 19 is described below.

Figure 6:
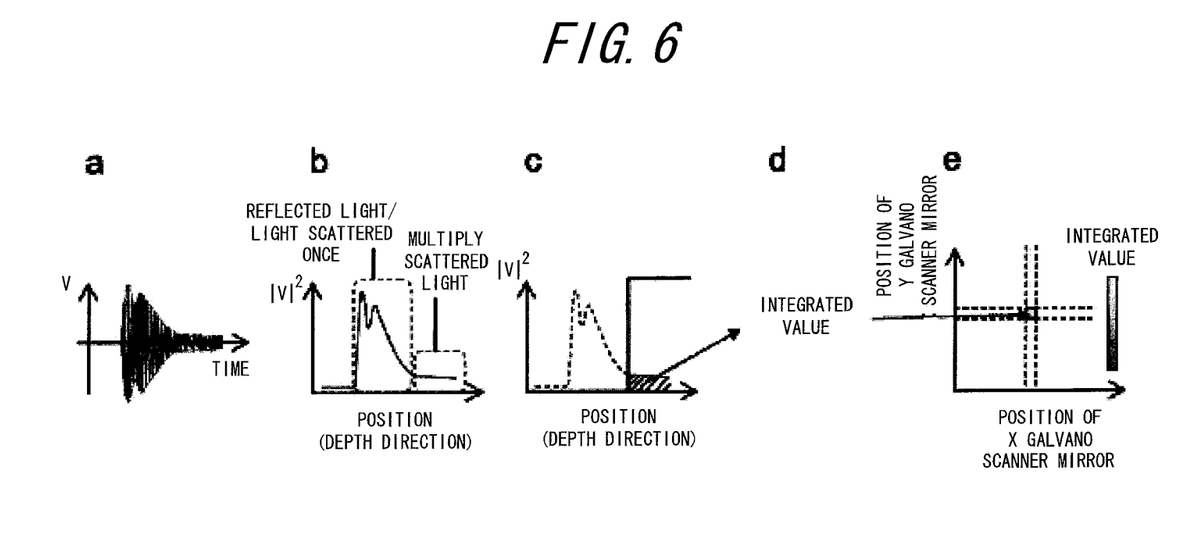
FIG. 6 is a schematic diagram illustrating a signal processing operation illustrated in FIG. 5.

With the configuration illustrated in FIG. 4, the signal conversion unit (time) 27 in FIG. 5 detects the envelope of the digital output signal from the AD converter 18 (FIG. 6, a) and further converts an amplitude signal thereof to a power signal. In doing so, time is converted from the relative delay time between the inspection light and the reference light and the sweeping rate of the sweeping reflective mirror 26 to the spatial distance in the depth direction of the object to be inspected 16 for output (FIG. 6, b). Since other means are similar to those illustrated in FIGS. 2 and 3, the same components are denoted by the same reference symbols, and the description thereof will be omitted.

Thus, by using this embodiment, it is possible to use a significantly inexpensive light source such as SLD, which makes it possible to realize the optical imaging system more inexpensively.

(Third Embodiment)

Figure 7:
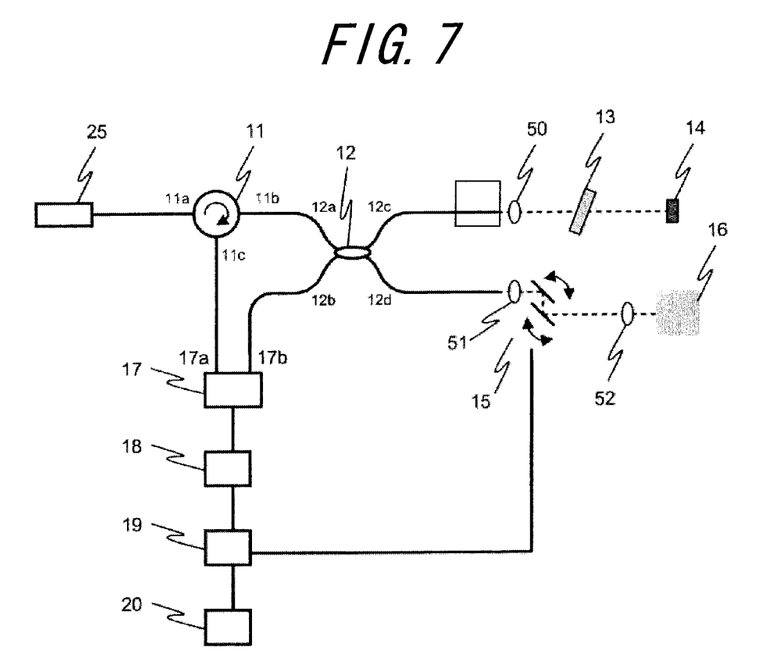
FIG. 7 is a block diagram illustrating a configuration of a main part of an optical imaging system according to a third embodiment of the present invention.

FIG. 7 is a block diagram illustrating a configuration of the optical imaging system according to a third embodiment of the present invention. FIG. 7 is similar to FIG. 4, except that the reflective mirror 14 is used in FIG. 7. The reflective mirror 14 is fixed in such a way that delay time of the reference light coincides with delay time of the multiply scattered light.

Since the configuration is otherwise similar to that illustrated in FIG. 4, the same components are denoted by the same reference symbols, and the description thereof will be omitted.

Figure 8:
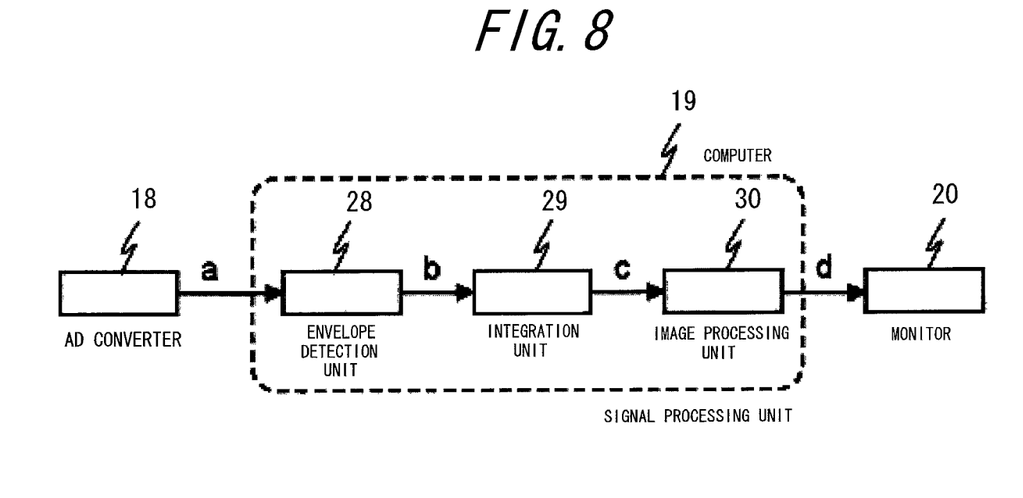
FIG. 8 is a functional block diagram illustrating signal processing performed by a computer illustrated in FIG. 7.

The signal processing performed by the computer 19 in FIG. 7 is illustrated in FIG. 8. Examples of the signal at points a to d in FIG. 8 are shown as a to d, respectively, in FIG. 9, and the signal processing performed by the computer 19 is described below.

Figure 9:
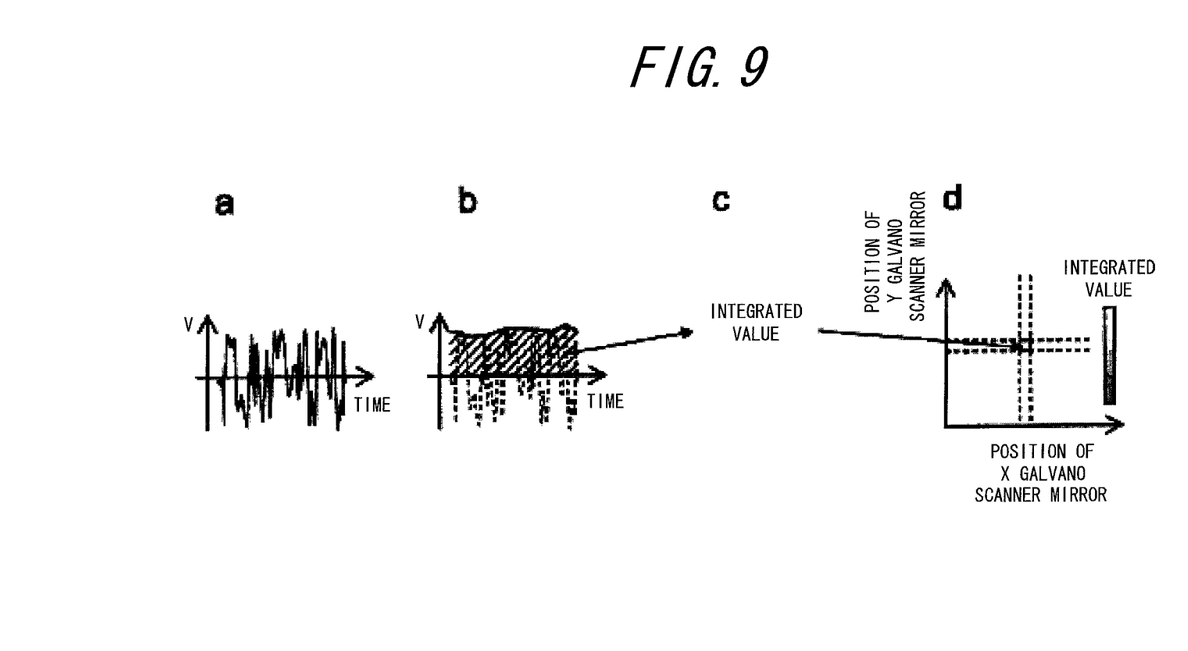
FIG. 9 is a schematic diagram illustrating a signal processing operation illustrated in FIG. 8.

The computer 19 performs the signal processing in an envelope detection unit 28, an integration unit 29, and an image processing unit 30. The envelope detection unit 28 detects (FIG. 9, b) the envelope of the digital output signal from the AD converter 18 (FIG. 9, a). The output of the envelope detection unit 28 is input to the integration unit 29. The integration unit 29 is operated to integrate the output of the envelope detection unit 28 (FIG. 9, b, shaded area), and outputs the integrated value (FIG. 9, c). The output signal from the integration unit 29 are input to the image processing unit 30. The image processing unit 30 assigns an output value from the integration unit 29 to each set value of the X-Y galvano scanner mirror 15, that is, each position on the object to be inspected 16 irradiated with the inspection light, and generates an image with information on the deep portion of the object to be inspected 16 (FIG. 9, d). Output from the image processing unit 30 are input to the monitor 20, as a result of which the image with information on the deep portion of the object to be inspected 16 is displayed on the monitor 20.

Thus, with this embodiment, it is possible to utilize a significantly inexpensive light source such as SLD and to eliminate the need for sweeping the reflective mirror on an optical path of the reference light, which makes it possible to realize the optical imaging system more inexpensively. Further, since it is not necessary to create an intensity distribution of the reflected and scattered light from the object to be inspected, the signal processing load can be reduced. In this way, high-speed image acquisition can be realized.

Although all embodiments of the optical imaging system described here use the Michelson interferometer configuration, it is appreciated that, for example, a dual-axes confocal microscope using a Mach-Zehnder interferometer configuration is applicable with a similar effect (see, Wang et al., Optics Letters, vol. 28, p. 1915 (2003)).

REFERENCE SIGN LIST 10 wavelength swept laser
11 optical circulator
12 optical coupler
13 optical attenuator
14 reflective mirror
15 X-Y galvano scanner mirror
16 object to be inspected
17 balanced receiver
18 analog-digital converter
19 computer
20 monitor
21 signal conversion unit (wavelength sweeping)
22 signal extraction unit
23 integration unit
24 image processing unit
25 super luminescent diode
26 movable reflective mirror
27 signal conversion unit (time)
28 envelope detection unit
29 integration unit
30 image processing unit
50 lens
51 lens
52 lens The inventions claimed is:
1. An optical imaging system comprising:
a light source configured to emit light;
a light reflector;
a light scanner mirror;
an optical multiplexer/demultiplexer, wherein the optical multiplexer/demultiplexer is configured to demultiplex the light emitted from the light source into inspection light and reference light,
wherein the light reflector is configured to reflect the reference light,
wherein the light scanner mirror is configured to scan the inspection light on an object to be inspected, and
wherein the optical multiplexer/demultiplexer is configured to multiplex reflected inspection light obtained by the inspection light being reflected and scattered by the object to be inspected and reflected reference light obtained by the reference light being reflected by the light reflector, so as to generate interference light;
a photoelectric conversion circuit configured to photoelectrically convert the interference light into an analog output signal;
an analog-digital converter configured to convert the analog output signal to a digital signal; and
a processor comprising hardware, wherein the processor is configured to:
  remove a signal resulting from the light reflected and scattered once by the object to be inspected from the digital signal, wherein the removed signal includes information on a surface portion of the object to be inspected, to thereby extract a signal resulting from multiply scattered light in the object to be inspected, wherein the extracted signal includes information on a deeper portion of the object to be inspected that is deeper than the surface portion;
  integrate the extracted signal to thereby generate an integrated signal; and
  generate an image of the object to be inspected on the basis of the integrated signal and positional information from the light scanner mirror.

2. The optical imaging system according to claim 1, wherein the light source comprises a wavelength swept laser.

3. The optical imaging system according to claim 2, wherein the processor is configured to:
  perform Fourier transform of the digital signal to thereby generate a signal representative of a signal intensity distribution with respect to a position in the object to be inspected; and
  extract the signal resulting from multiply scattered light in the object to be inspected from the signal representative of the signal intensity distribution with respect to the position in the object to be inspected as the extracted signal.

4. The optical imaging system according to claim 1, wherein the light source comprises a super luminescent diode or pulse light source, and
wherein the light reflector is configured to be driven to sweep over relative delay time between the inspection light and the reference light.

5. The optical imaging system according to claim 4, wherein the processor is configured to: detect an envelope of the digital signal to remove the signal resulting from the light reflected and scattered once by the object to be inspected from the digital signal.

6. The optical imaging system according to claim 1, wherein the light source comprises a super luminescent diode or pulse light source, and
wherein the light reflector is configured such that delay time of the reference light coincides with delay time of the multiply scattered light.

7. The optical imaging system according to claim 6, wherein the processor is configured to detect an envelope of the digital signal to remove the signal resulting from the light reflected and scattered once by the object to be inspected from the digital signal.

8. The optical imaging system according to claim 1, wherein the photoelectric conversion circuit is configured to perform balanced detection.

9. An endoscope comprising:
the optical imaging system according to claim 1,
wherein the object to be inspected is the inside of a body cavity.

10. A microscope comprising:
the optical imaging system according to claim 1.

11. An optical imaging method comprising:
emitting, with a light source, a light;
demultiplexing, with an optical multiplexer/demultiplexer, the light emitted from the light source into inspection light and reference light;
reflecting, with a light reflector, the reference light;
scanning, with a light scanner mirror, the inspection light on an object to be inspected;
multiplexing, with the optical multiplexer/demultiplexer, reflected inspection light obtained by the inspection light being reflected and scattered by the object to be inspected and reflected reference light obtained by the reference light being reflected by the light reflector so as to generate interference light;
photoelectrically converting, with the photoelectric conversion circuit, the interference light into an analog output signal;
converting, with an analog-digital converter, the analog output signal into a digital signal;
removing, with a processor comprising hardware, a signal resulting from the light reflected and scattered once by the object to be inspected from the digital signal, wherein the removed signal includes information on a surface portion of the object to be inspected, to thereby extract a signal resulting from multiply scattered light in the object to be inspected, wherein the extracted signal includes information on a deeper portion of the object to be inspected that is deeper than the surface portion;
integrating, with the processor, the extracted signal to thereby generate an integrated signal; and
generating, with the processor, an image of the object to be inspected on the basis of the integrated signal and positional information from the light scanner mirror.

* * * * *